United States Patent [19] [11] 4,086,350
Zirkle [45] Apr. 25, 1978

[54] PHARMACEUTICAL COMPOSITIONS AND METHOD OF PRODUCING ANTI-PSYCHOTIC ACTIVITY WITHOUT EXTRAPYRAMIDAL SYMPTOMS

[75] Inventor: Charles Leon Zirkle, Berwyn, Pa.

[73] Assignee: SmithKline Corporation, Philadelphia, Pa.

[21] Appl. No.: 655,587

[22] Filed: Feb. 5, 1976

Related U.S. Application Data

[63] Continuation-in-part of Ser. No. 521,216, Nov. 6, 1974, abandoned.

[30] Foreign Application Priority Data

Oct. 16, 1975 South Africa ........................ 75/6550

[51] Int. Cl.$^2$ ................. A61K 31/445; C07D 405/04; C07D 409/04
[52] U.S. Cl. ............................... 424/267; 260/293.58; 260/293.57
[58] Field of Search ................... 424/267; 260/293.57, 260/293.58

[56] References Cited

U.S. PATENT DOCUMENTS

| 3,055,903 | 9/1962 | Renz et al. | 260/293.4 |
| 3,275,640 | 9/1966 | Engelhardt et al. | 260/293.4 |
| 3,470,188 | 9/1969 | Kaiser et al. | 260/293.4 |

OTHER PUBLICATIONS

Kaiser et al., J. Med. Chem. 17 (1), 57–62 (1974).

*Primary Examiner*—John M. Ford
*Attorney, Agent, or Firm*—Richard D. Foggio; William H. Edgerton

[57] ABSTRACT

Tricyclic piperidylidene derivatives administered internally to an animal host, in therapeutically effective amounts, produce antipsychotic activity without extrapyramidal symptoms. Certain of the active ingredients are novel compounds per se.

17 Claims, No Drawings

PHARMACEUTICAL COMPOSITIONS AND METHOD OF PRODUCING ANTI-PSYCHOTIC ACTIVITY WITHOUT EXTRAPYRAMIDAL SYMPTOMS

This application is a continuation-in-part of application Ser. No. 521,216 filed Nov. 6, 1974, now abandoned.

This invention relates to novel pharmaceutical compositions containing as an active ingredient compounds which produce antipsychotic activity without extrapyramidal symptoms and to a method of producing antipsychotic activity without extrapyramidal symptoms which comprises administering nontoxic effective quantities of said active ingredients to an animal. Extrapyramidal symptoms (EPS) are some of the most undesirable and common side-effects produced by antipsychotic or neuroleptic drugs. The compounds which are the active ingredients used in the compositions and methods of this invention have a neuropharmacological profile indicative of potent antipsychotic activity but essentially no liability to produce EPS.

The active ingredients used in the compositions and methods of this invention are piperidylidene derivatives of xanthene, thioxanthene and dibenzozepin of the following general formulas:

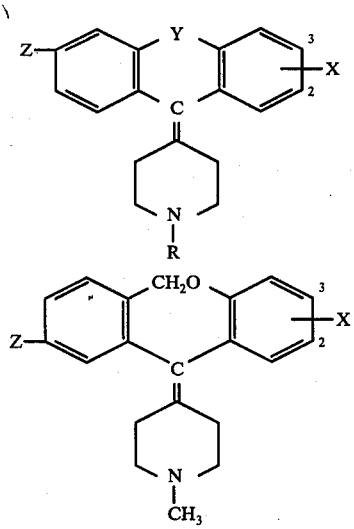

FORMULA I

FORMULA II wherein, for formula I:
when Y represents oxygen, X is 2-chloro, 2-fluoro, 2-trifluoromethyl, 2-thiomethyl, 2-bromo or 2-cyano, Z is hydrogen and R is methyl;

when Y represents oxygen, X is 2-chloro, Z is hydrogen and R is hydrogen, ethyl, β-hydroxyethyl, n-propyl, 3-hydroxypropyl or cyclobutylmethyl;

when Y represents oxygen, X is 2-bromo, Z is hydrogen and R is hydrogen, β-hydroxyethyl or n-butyl;

when Y represents oxygen, X is 2-trifluoromethyl, Z is hydrogen an R is n-butyl;

when Y represents sulfur, X is 2- or 3-chloro, 2-thiomethyl, 2- or 3-fluoro, 2-bromo or 2-cyano, Z is hydrogen and R is methyl;

when Y represents sulfur, X is 2-chloro, Z is hydrogen and R is β-hydroxyethyl, ethyl, n-butyl or cyclobutylmethyl; and when Y represents oxygen, X is 2-fluoro, Z is 6-chloro and R is methyl;

when Y represents sulfur, X is 2-fluoro, Z is 6-chloro or 6-fluoro and R is methyl; and
for formula II:
when X is 2- or 3-chloro, Z is hydrogen; and
when X is hydrogen, Z is 9-chloro.

Preferred compounds for use as active ingredients are those of formula I wherein Y is oxygen, X is 2-chloro, Z is hydrogen and R is methyl, and of formula II wherein X is hydrogen and Z is 9-chloro.

Certain of the compounds of formulas I and II are novel compounds and as such form a part of this invention. These compounds are as follows:
in formula I,
when Y represents oxygen, X is 2-chloro, 2-fluoro, 2-bromo, 2-thiomethyl or 2-cyano, Z is hydrogen and R is methyl;

when Y represents oxygen, X is 2-fluoro, Z is 6-chloro and R is methyl;

when Y represents oxygen, X is 2-chloro, Z is hydrogen and R is hydrogen, ethyl, β-hydroxyethyl, n-propyl or 3-hydroxypropyl;

when Y represents oxygen, X is 2-bromo, X is hydrogen and R is hydrogen, β-hyroxyethyl or n-butyl;

when Y represents oxygen, X is 2-trifluoromethyl, Z is hydrogen and R is n-butyl;

when Y represents sulfur, X is 2-cyano, Z is hydrogen and R is methyl; and
in formula II:
when X is hydrogen, Z is 9-chloro.

The nontoxic pharmaceutically acceptable acid addition salts of the compounds of formulas I and II are similarly useful in the compositions and methods of this invention. Such salts are easily prepared by methods known to the art. The base is reacted with either the calculated amount of organic or inorganic acid in aqueous miscible solvent, such as acetone or ethanol, with isolation of the salt by concentration and cooling or an excess of the acid in aqueous imiscible solvent, such as ethyl ether or chloroform, with the desired salt separating directly. Exemplary of such organic salts are thoe with maleic, fumaric, benzoic, ascorbic, pamoic, succinic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids as well as with 8-halotheophyllines, for example 8-bromotheophylline. Exemplary of such inorganic salts are those with hydrochloric, hydrobromic, sulfuric, cyclohexylsulfamic, phosphoric and nitric acids. Of course, these salts may also be prepared by the classical method of double decomposition of appropriate salts which is well known to the art.

The compounds of formulas I and II where R is methyl are generally prepared from an appropriately substituted xanthone, thioxanthone or dibenzoxepinone by reaction with an N-methylpiperidyl magnesium halide in an inert organic solvent such as ether, for example ethyl ether, dioxane or tetrahydrofuran, at from room temperature to the reflux temperature of the solvent, for from 30 minutes to 4 hours. The tricyclic carbinol intermediate is dehydrated to the olefin under acid or thermal conditions.

To prepare the compounds of formula I where R is other than methyl, the N-methylpiperidylidene derivative is treated with cyanogen bromide to give the N-cyanamide which is treated with acid to obtain the N-unsubstituted derivatives. The latter are N-alkylated by one of the following methods:

a. direct alkylation with the appropriate alkyl bromide;

b. acylation with the appropriate acyl chloride to the corresponding amides followed by lithium aluminun hydride reduction; or c. reaction with ethylene oxide.

U.S. Pat. Nos. 3,275,640 and 3,055,903 disclose piperidylidene thioxanthenes; South African Pat. No. 67/04371 discloses piperidylidene dibenzoxepin; and U.S. Pat. No. 3,470,188 discloses piperidylidene xanthenes and thioxanthenes, however, none of these or equivalent prior art disclose the unique feature of the compounds of formula I, namely antipsychotic activity with no EPS. Belgian Pat. No. 808,347 describes dinuclear substituted thioxanthenes having a heterocyclic propyl or propylidene side chain as neuroleptics with reduced extrapyramidal symptoms.

There is evidence that antipsychotic drugs cause EPS by interfering with neurotransmission in a nigrostriatal dopaminergic pathway. It is thought that they block dopamine receptors in the neostriatum. Therefore, the ability of a drug to block striatal dopamine receptors is a measure of its EPS liability.

To assess the potency of drugs in blocking striatal dopamine receptors a procedure was used which was developed by Ungerstedt [Ungerstedt and Arbuthnott, Brain Res. 24 485 (1970); Ungerstedt, Acta physiol. scand., Suppl. 367, 49 (1971)] using rats with unilateral lesions of the substantia nigra induced by injection of 6-hydroxydopamine. This treatment causes degeneration of the nigrostriatal dopaminergic pathway accompanied by a marked decrease in the dopamine content of the neostriatum on the side of the lesion. Animals with this lesion develop postural and motor asymmetries which are altered by drugs which affect dopaminergic activity. Amphetamine, which releases dopmine and norepinephrine from catecholaminergic neurons, causes these rats to rotate unidirectionally toward the side of the lesion. Since there is a much larger amount of dopamine to be released by amphetamine from the intact nigrostriatal neurons on the non-lesioned side than from those remaining on the lesioned side, the rotational behavior is apparently due to the preponderance of activation of striatal dopamine receptors on the intact side. The ability of a drug to antagonize the rotational behavior is therefore a measure of its ability to block striatal dopamine receptors and is indicative of its potential to produce EPS.

To predict the potential ability of a drug to cause EPS, the ratio of its $ED_{50}$ (i.p.) for antagonism of amphetamine-induced rotation to its $ED_{50}$ (i.p.) for blockade of shock avoidance acquisition in the rat, a procedure for assessing antipsychotic activity, (R/A ratio) is calculated. The $ED_{50}$ values of some clinically established antipsychotics in the avoidance and rotational tests and the R/A ratios are presented in Table I. Chlorpromazine has a R/A ratio of 1.3. Antipsychotics that have a considerably greater propensity to cause EPS than chlorpromazine, e.g., trifluoperazine, haloperidol and pimozide, have ratios of 0.3 to 0.5. The two antipsychotics known to produce EPS to a lesser extent than chlorpromazine, i.e. thioridazine and clozapine, have ratios of 2.7 and 3.8, respectively. Therefore a high R/A ratio predicts that a drug will have a low potential to produce EPS.

Table I

| Drug | A<br>Antagonism of<br>Avoidance<br>Acquisition<br>Rats<br>$ED_{50}$ mg/kg (i.p.) | R<br>Antagonism of<br>Amphetamine-induced<br>Rotation<br>Rats<br>$ED_{50}$ mg/kg (i.p.) | R/A |
|---|---|---|---|
| Chlorpromazine | 1.5 | 2.0 | 1.3 |
| Trifluoperazine | 0.26 | 0.12 | 0.46 |
| Haloperidol | 0.16 | 0.05 | 0.31 |
| Pimozide | 0.24 | 0.08 | 0.30 |
| Thioridazine | 5.1 | 13.7 | 2.7 |
| Clozapine | 6.6 | 25.4 | 3.8 |

The specific piperidylidene derivatives of formulas I and II having a large R/A ratio and therefore should be essentially free of EPS liability are listed below:

I. 4-(2-chloro-9-thioxanthenylidene)-1-methylpiperidine

II. 1-methyl-4-(2-methylthio-9-thioxanthenylidene)-piperidine

III. 4-(3-chloro-9-thioxanthenylidene)-1-methylpiperidine

IV. 4-(2-chloro-9-xanthenylidene)-1-methylpiperidine

V. 1-methyl-4-(2-methylthio-9-xanthenylidene)-piperidine

VI. 1-methyl-4-(2-trifluoromethyl-9-xanthenylidene)-piperidine

VII. 4-(2-chloro-11(6H)-dibenz[b,e]oxepinylidene)-1-methylpiperidine

VIII. 4-(2-fluoro-9-xanthenylidene)-1-methylpiperidine

IX. 4-(2-chloro-9-thioxanthenylidene)-1-(β-hydroxyethyl)piperidine.

X. 4-(2-bromo-9-xanthenylidene)-1-methylpiperidine

XI. 4-(2-cyano-9-xanthenylidene)-1-methylpiperidine

XII. 4-(2-fluoro-9-thioxanthenylidene)-1-methylpiperidine

XIII. 4-(3-fluoro-9-thioxanthenylidene)-1-methylpiperidine

XIV. 4-(2-bromo-9-thioxanthenylidene)-1-methylpiperidine

XV. 4-(6-chloro-2-fluoro-9-thioxanthenylidene)-1-methylpiperidine

XVI. 4-(6-chloro-2-fluoro-9-xanthenylidene)-1-methylpiperidine

XVII. 4-(2-chloro-9-thioxanthenylidene)-1-ethylpiperidine

XVIII. 4-(2-chloro-9-thioxanthenylidene)-1-n-butylpiperidine

XIX. 4-(2-chloro-9-thioxanthenylidene)-1-cyclobutylmethylpiperidine

XX. 4-(2-chloro-9-xanthenylidene)-piperidine

XXI. 4-(2-chloro-9-xanthenylidene)-1-ethylpiperidine

XXII. 4-(2-chloro-9-xanthenylidene)-1-(β-hydroxyethyl)-piperidine

XXIII. 4-(2-chloro-9-xanthenylidene)-1-n-propylpiperidine

XXIV. 4-(2-chloro-9-xanthenylidene)-1-cyclobutylmethylpiperidine

XXV. 4-(2-bromo-9-xanthenylidene)-piperidine

XXVI. 4-(2-bromo-9-xanthenylidene)-1-(β-hydroxyethyl)-piperidine

XXVII. 4-(9-chloro-11(6H)-dibenz[b,e]oxepinylidene)-1-methylpiperidine

XXVIII. 4-(2-cyano-9-thioxanthenylidene)-1-methylpiperidine

XXIX. 4-(2,6-difluoro-9-thioxanthenylidene)-1-methylpiperidine

XXX. 4-(2-chloro-9-xanthenylidene)-1-(3-hydroxypropyl)-piperidine

XXXI. 4-(2-trifluoromethyl-9-xanthenylidene)-1-n-butylpiperidine

XXXII. 4-(2-bromo-9-xanthenylidene)-1-n-butylpiperidine

XXXIII. 4-(3-chloro-11(6H)-dibenz[b,e]oxepinylidene)-1-methylpiperidine.

The $ED_{50}$ values of these compounds in the avoidance acquisition and rotational tests and their R/A ratios are presented in Table II.

Table II

| Compound | A<br>Antagonism of<br>Avoidance<br>Acquisition<br>Rats<br>$ED_{50}$ mg/kg (i.p.) | R<br>Antagonism of<br>Amphetamine-induced<br>Rotation<br>Rats<br>$ED_{50}$ mg/kg (i.p.) | R/A |
|---|---|---|---|
| I | 0.7 | 14.2 | 20.3 |
| II | 0.2 | 3.7 | 18.5 |
| III | 5.3 | 30.8 | 5.8 |
| IV | 0.23 | 2.8 | 12.2 |
| V | 0.6 | 1.8 | 3.0 |
| VI | 0.07 | 0.26 | 3.7 |
| VII | 1.7 | 9.4 | 5.5 |
| VIII | 0.71 | 5.6 | 7.9 |
| IX | 0.26 | 1.22 | 4.7 |
| X | 0.3 | 1.6 | 5.3 |
| XI | 0.09 | 0.29 | 3.2 |
| XII | 1.8 | 5.5 | 3.1 |
| XIII | 3.0 | 17.7 | 5.8 |
| XIV | 0.3 | 2.7 | 9.0 |
| XV | 0.6 | 8.7 | 14.5 |
| XVI | 0.15 | 1.12 | 7.5 |
| XVII | 0.5 | 5.0 | 10.0 |
| XVIII | 0.94 | 3.1 | 3.3 |
| XIX | 0.5 | 1.9 | 3.8 |
| XX | 1.7 | 8.1 | 4.8 |
| XXI | 0.5 | 1.8 | 3.6 |
| XXII | 0.2 | 1.3 | 6.5 |
| XXIII | 0.6 | 2.4 | 4.0 |
| XXIV | 0.5 | 1.6 | 3.2 |
| XXV | 0.6 | 4.0 | 6.7 |
| XXVI | 0.6 | 2.1 | 3.5 |
| XXVII | 1.6 | >24 | >15 |
| XXVIII | 0.16 | 0.67 | 4.0 |
| XXIX | 0.5 | 2.4 | 4.8 |
| XXX | 0.2 | 0.78 | 3.9 |
| XXXI | 0.1 | 1 | 10 |
| XXXII | 0.6 | 3.0 | 5.0 |
| XXXIII | 7.5 | >25 | >3 |

The compositions of this invention are prepared in conventional dosage unit forms by incorporating a compound of formulas I or II or a pharmaceutically acceptable salt thereof, in a nontoxic amount sufficient to produce antipsychotic activity without extrapyramidal symptoms in an animal, with a nontoxic pharmaceutical carrier according to accepted procedures. Preferably the compositions will contain the active ingredient in an active but nontoxic amount selected from about 1 mg. to about 300 mg., advantageously from about 5 mg. to about 200 mg., of active ingredient per dosage unit.

The pharmaceutical carrier employed may be, for example, either a solid or liquid, giving rise to a wide variety of pharmaceutical forms. If a solid pharmaceutical carrier is used, such as lactose, magnesium stearate, terra alba, sucrose, talc, stearic acid, gelatin, agar, pectin, acacia and the like, the composition can be tableted, used as a pharmaceutical powder, placed in a hard gelatin capsule or in the form of a troche or lozenge. The amount of solid carrier will vary widely but preferably will be from about 25 mg. to about 1 g. If a liquid pharmaceutical carrier is used, such as syrup, peanut oil, olive oil, sesame oil, water and the like, the composition will be in the form of a soft gelatin capsule, syrup, emulsion or a liquid suspension. Similarly the carrier or diluent may include a time delay material such as glyceryl monostearate or glyceryl distearate alone or with a wax.

Parenteral dosage forms such as for intramuscular administration are obtained by dissolving a water soluble salt of the active medicament in water or saline solution in a concentration such that 1 cc. of the solution contains from about 2 mg. to about 50 mg. of active ingredient. The solution can then be filled into single ampuls or multiple dose vials.

In accordance with the method of this invention a compound of formula I or II or a nontoxic acid addition salt thereof is administered internally to an animal in need of antipsychotic activity, preferably with a pharmaceutical carrier, in a nontoxic amount sufficient to produce antipsychotic activity without extrapyramidal symptoms. The active medicament, preferably in a dosage unit, is administered orally or intramuscularly in an active, nontoxic quantity selected from about 1 mg. to about 300 mg. of the parent chemical of formula I or II. Advantageously equal doses will be administered until a desired effect is obtained, such as two or three times a day. The daily dosage is selected from about 2 mg. to about 900 mg. of active medicament, advantageously from about 10 mg. to about 600 mg. When the method described above is carried out, antipsychotic activity is obtained with minimal EPS.

The following examples illustrate specific pharmaceutical compositions and their use in accordance with the method of this invention and as such are not to be considered as limitations thereof.

EXAMPLE 1

| Ingredients | Mg. per capsule |
|---|---|
| 4-(2-chloro-9-thioxanthenylidene-1-methylpiperidine (as an acid addition salt) | 50 (free base) |
| Magnesium stearate | 2 |
| Lactose | 200 |

The above ingredients are mixed, passed through a #40 mesh screen, remixed and filled into #2 capsules.

EXAMPLE 2

| Ingredients | W/V percentages |
|---|---|
| 4-(2-chloro-9-xanthenylidene)-1-methylpiperidine (as a water soluble acid addition salt) | Equivalent to 20 mg. of free base per ml. |
| Sodium tartrate | 1 |
| Tartaric acid | 0.7 |
| Water for parenterals, q.s. | 100 |

The above ingredients are dissolved in an amount of the water equal to approximately 95% of the final volume, mixed, heated as required, cooled to room temperature and the remainder of water is added. The solution is filtered and filled in ampuls.

The capsules or solution prepared as in Examples 1 or b 2 are administered internally to an animal requiring antipsychotic activity within the dose ranges set forth hereinabove. Similarly other compounds of formulas I or II can be formulated in the same manner to give pharmaceutical compositions useful in the methods of this invention.

EXAMPLE 3

To 4.3 g. (0.175 m.) of magnesium turnings just covered with dry tetrahydrofuran at gentle reflux under nitrogen is added 1 ml. of a tetrahydrofuran solution of the base derived from 29.8 g. (0.175 m.) of 4-chloro-N-methylpiperidine hydrochloride (base in about 50 ml. of tetrahydrofuran). (The base was previously liberated by use of ether, potassium hydroxide pellets, 1 ml. of water, triturating, extracting with ether and evaporating in vacuo the dried ether solution.) A small amount of ethereal methyl magnesium bromide is added and when the reaction starts the remainder of the base is diluted with about 150 ml. of tetrahydrofuran while stirring. This solution is added dropwise over one-half hour while maintaining low heat and the resulting mixture is refluxed and stirred for one hour. At low reflux 27.0 g. (0.117 m.) of 2-chloroxanthone is added portionwise with stirring. The reaction mixture is stirred and refluxed for one hour and then quenched on a mixture of ice-water ammonium chloride to give an oil which solidified. Recrystallization from ethyl acetate gives 2-chloro-9-(1-methyl-4-piperidyl)-xanthene-9-ol, m.p. 206°–208° C.

A mixture of 12.5 g. (0.038 m.) of the xanthene-9-ol, 14.0 g. (0.76 m.) of o-sulfobenzoic anhydride and 380 ml. of propionic acid is refluxed for three hours. The reaction mixture is heated in vacuo at 100° C. and the resulting syrup is dissolved in water, made strongly basic with 40% sodium hydroxide solution, extracted with ether, and the dried extract is evaporated. The residual free base is dissolved in ethyl acetate and maleic acid (4.4 g.) is added to yield 4-(2-chloro-9-xanthenylidene)-1-methylpiperidine maleate, m.p. 206°–207° C.

EXAMPLE 4

The Grignard reagent from 68 g. (0.4 m.) of 4-chloro-N-methylpiperidine hydrochloride and 9.7 g. (0.4 m.) of magnesium turnings in a total volume of 250 ml. of tetrahydrofuran is obtained following the procedure of Example 3. After all the halide is added, 75.6 g. (0.287 m.) of 2-trifluoromethylxanthone is added portionwise and refluxing/stirring are continued for one hour under nitrogen. The reaction mixture is quenched on ice-water-ammonium chloride to give 9-(1-methyl-4-piperidyl)-2-trifluoromethylxanthene-9-ol, m.p. 179°–183° C.

Dehydration of the xanthene-9-ol (88.2 g., 0.24 m.) is accomplished by refluxing with 88.1 g. (0.48 m.) of sulfobenzoic anhydride and 1.2 l. of propionic acid for two hours. The reaction mixture is heated in vacuo at 100° C. and the residual syrup is dissolved in water and made strongly basic with 40% sodium hydroxide solution. Extraction with ether gives 1-methyl-4-(2-trifluoromethyl-9-xanthenylidene)-piperidine, m.p. 82°–83° C.

EXAMPLE 5

Following the procedure of Example 3, the Grignard reagent formed from 2.4 g. (0.1 m.) of magnesium and 13.3 g. (0.1 m.) of 4-chloro-N-methylpiperidine is reacted with 12.1 g. (0.05 m.) of 2-thiomethylxanthone to give 9-(1-methyl-4-piperidyl)-2-thiomethylxanthene-9-ol, m.p. 169° C.

The xanthene-9-ol (10.8 g., 0.032 m.) thus prepared is dehydrated by refluxing with 11.6 g. (0.064 m.) of sulfobenzoic anhydride and 258 ml. of propionic acid. After work-up of the reaction mixture, extraction with methylene chloride followed by addition of ether precipitates unreacted xanthene-9-ol which is removed by filtration. The filtrate is concentrated to give an oil which is converted in ether to the maleate salt of 1-methyl-4-(2-methylthio-9-xanthenylidene)-piperidine, m.p. 172°–180° C.

EXAMPLE 6

The Grignard reagent prepared from 0.53 g. (0.0216 m.) of magnesium and 2.9 g. (0.0216 m.) of 4-chloro-N-methylpiperidine is reacted with 2.3 g. (0.0108 m.) of 2-fluoroxanthone as described in Example 3. The reaction mixture is heated for four hours and then decomposed with saturated ammonium chloride solution to yield 2-fluoro-9-(1-methyl-4-piperidyl)-xanthene-9-ol, m.p. 193°–200° C.

A mixture of 0.58 g. (0.002 m.) of the above prepared xanthene-9-ol, 0.34 g. (0.004 m.) of sulfobenzoic anhydride and 20 ml. of propionic acid is refluxed for about 15 minutes and then stirred without heating until cooled. The reaction mixture is evaporated in vacuo and the residue is taken up in methylene chloride. The product is treated with maleic acid to afford the maleate salt of 4-(2-fluoro-9-xanthenylidene)-1-methylpiperidine, m.p. 189°–193° C.

EXAMPLE 7

To a solution of 13.2 g. (0.0318 m.) of 4-(2-chloro-9-thioxanthenylidene)-piperidine in 50 ml. of methanol at 50° C. is added a solution of 2.2 g. (0.0383 m.) of ethylene oxide in 30 ml. of methanol over ten minutes and the mixture is refluxed for one and one-half hours. After standing overnight at room temperature, the reaction mixture is filtered to yield 4-(2-chloro-9-thioxanthenylidene)-1-($\beta$-hydroxyethyl)-piperidine, m.p. 178°–180° C.

EXAMPLE 8

To a stirred suspension of 2.43 g. (0.1 g.-atom) of magnesium turnings in 5 ml. of tetrahydrofuran under nitrogen is added several drops of ethyl bromide. After the reaction is started, 13.4 g. (0.1 mole) of 4-chloro-1-methylpiperidine in 50 ml. of tetrahydrofuran is added at a rate sufficient to cause reflux. The mixture is stirred and refluxed for one hour, then it is cooled to 0° C. and 20.6 g. (0.075 mole) of 2-bromoxanthone is added in portions. The stirred mixture is refluxed for four hours and then it is poured into a solution of 26.5 g. (0.5 mole) of ammonium chloride in 500 ml. of ice-water. The crystalline alcohol, 2-bromo-9-(1-methyl-4-piperidyl)-xanthene-9-ol, m.p. 201°–202°, is filtered.

The above alcohol 20.0 g. (0.053 mole) is dissolved in 200 ml. of propionic acid and 20.0 g. (0.011 mole) of sulfobenzoic anhydride. The solution is refluxed for one hour, concentrated in vacuo, and then the residue is diluted with water. The mixture is made alkaline with 2.5 N sodium hydroxide and extracted with ether. The ether extracts are dried and concentrated to give 4-(2-bromo-9-xanthenylidene)-1-methylpiperidine, which identified as its maleate salt, m.p. 206° C. (dec.).

EXAMPLE 9

To a stirred solution of 7.0 g. (0.065 mole) of cyanogen bromide in 150 ml. of benzene at 50°–55° C. is added 19.5 g. (0.055 mole) of 4-(2-bromo-9-xanthenylidene)-1-methylpiperidine in 150 ml. of benzene. The solution is heated for 2.5 hours, then it is concentrated in vacuo. The residue is dissolved in methylene chloride and the solution is washed with 1N hyrochloric acid, water and a saturated aqueous solution of sodium chloride. The organic solution is concentrated to give a semi-crystalline residue which is refluxed for 16 hours with a solution of 225 ml. of acetic acid and 25 ml. of 12N hyrochloric acid in 125 ml. of water. The solution is concentrated and the residue is dissolved in water. After the solution is made alkaline with sodium hydroxide, the mixture is extracted with ethyl acetate. The extracts are concentrated and a solution of the crystalline residue in acetonitrile is treated with methanesulfonic acid in acetonitrile-ether to give colorless crystals, m.p. 257.5°–258.5° C., of 4-(2-bromo-9xanthenylidene) piperidine methanesulfonate.

EXAMPLE 10

To 1.2 l g. (0.05 mol) of magnesium turnings covered by tetrahydrofuran in an Argon atmosphere is added about 0.5 g. of 4-chloro-N-methylpiperidine (from 8.5 g., 0.025 mol of the hydrochloride salt) and a small amount of ethyl bromide. The mixture is heated until the reaction is initiated, the remainder of the chloro compound in about 20 ml. of tetrahydrofuran is added and the mixture is refluxed for four hours. 2-Bromothioxanthone (7.3 g., 0.025 mol) is added and the mixture is refluxed for five hours, and then stirred at room temperature 3 days. The reaction mixture is poured into aqueous ammonium chloride and filtered to give 2-bromo-9(1-methyl-4-piperidyl)thioxanthene-9-ol, m.p. 225.5°–226° C.

A solution of 4.0 g. (0.0103 mol) of 2-bromo-9-(1-methyl-4-piperidyl)-thioxanthene-9-ol in 20 ml. of concentrated hydrochloric acid is refluxed for 1.5 hours. The reaction mixture is evaporated to dryness and redissolved in water. The aqueous solution is washed with ether, basified and extracted with ether. The dried extract is evaporated and the residue in acetonitrile is treated with methanesulfonic acid to yield 4-(2-bromo-9-thioxanthenylidene)-1-methylpiperidine methanesulfonate, m.p. 210°–212° C. (dec.).

EXAMPLE 11

To a solution of 4-(2-bromo-9-xanthenylidine)piperidine (2.5 g., 0.0073 mol) in 50 ml. of ethanol, cooled to ca 0° C. is added excess ethylene oxide (1.1 ml., 0.022 mol.). The reaction mixture is kept at 0° C. After 30 minutes the ice-bath is removed and after an additional 2.5 hours, a thick white precipitate is formed which is filtered to give 4-(2-bromo-9-xanthenylidene)-1-(β-hydroxyethyl)piperidine, m.p. 142°–146° C.; methanesulfonate salt, m.p. 247°–248° C.

EXAMPLE 12

To a stirred solution of 5.4 g. (0.051 mol) of cyanogen bromide in 30 ml. of benzene at 50° C. is added gradually a solution of 14.7 g. (0.0426 mol) of 4-(2-chloro-9-thioxanthenylidene)-1-methylpiperidine in 70 ml. of benzene. The solution is heated at 50° C. and stirring continued for 1.5 hours. Excess water is added and the solution is extracted with dilute hydrochloric acid. The benzene is evaporated in vacuo and the crude cyanamide (14.9 g) is refluxed with 12.4 g. (0.22 mol) of potassium hydroxide in 125 ml. of 70% aqueous ethanol for 24 hours. The reaction mixture is evaporated in vacuo, water is added and extracted with ether. Etheral hydrogen chloride is added to form a hydrochloride salt which is then treated with base to liberate 4-(2-chloro-9-thioxanthenylidene)piperidine.

A solution of 0.8 g. (0.01 mol) of acetyl chloride in 10 ml. of benzene is added to 6.3 g. (0.02 mol) of the above-prepared piperidine in 30 ml. of benzene and the mixture refluxed for one hour. The cooled reaction mixture is extracted with water, then dilute acetic acid. The organic layer is washed with dilute sodium bicarbonate until neutral and then evaporated in vacuo. The oil residue (intermediate amide) is dissolved in ether, dried and gradually added to a suspension of 1.5 g. (0.04 mol) of lithium aluminum hydride in 50 ml. of ether. The mixture is stirred at room temperature for 24 hours, treated cautiously with 2.1 ml. of water and filtered. The filtrate is treated with ethereal hydrogen chloride to give 4-(2-chloro-9-thioxanthenylidene)-1-ethylpiperidine hydrochloride, m.p. 253° C. (dec.).

Similarly, 6.3 g. (0.02 mol) of 4-(2-chloro-9-thioxanthenylidene)piperidine in 30 ml. of benzene is treated with a solution of 1.2 g. (0.01 mol) of cyclobutylcarboxylic acid chloride in 10 ml. of benzene. Following the above workup procedure, the intermediate amide is reduced with 1.5 g. (0.04 mol) of lithium aluminum hydride in 50 ml. of ether. After isolation of the amine product, the ether is evaporated in vacuo and a hexamate salt formed of 4-(2-chloro-9-thioxanthenylidene)-1-cyclobutylmethylpiperidine, m.p. 180°–182° C.

Following the procedures as described above, 4-(chloro-9-thioxanthenylidene)piperidine (6.3 g., 0.02 mol) in 30 ml. of benzene is reacted with 1.0 g. (0.01 mol) of butyryl chloride in 10 ml. of benzene, followed by reduction of the intermediate amide with 1.5 l g. (0.04 mol) of lithium aluminum hyride to yield as a final product, 4-(2-chloro-9-thioxanthenylidene)-1-butylpiperidine hydrochloride, m.p. 259° C. (dec.).

EXAMPLE 13

Sodium hydride (1.0 mol) is suspended in about 300 ml. of dimethylformamide and phenol (1.0 mol) in about 200 ml. of dimethylformamide is added dropwise, keeping the reaction temperature around 25° C. The mixture is stirred until hydrogen evolution is completed. 6-Chlorophthalide (1.0 mol) in about 250 ml. of dimethylformamide is then added slowly. The resulting mixture is refluxed for 2 hours and allowed to stand at room temperature overnight. The reaction mixture is diluted with ice/water and extracted several times with ether. The aqueous fraction is acidified with dilute hydrochloric acid and extracted with ether. The ether is dried and concentrated to a gummy solid which is recrystallized from a minimum volume of alcohol to give 2-phenoxymethyl-5-chlorobenzoic acid, m.p. 149°–155° C.

A mixture of 1.0 mol. of the above prepared benzoic acid, supercel (570 g.) and xylene (about 2200 ml.) is stirred and about 300 ml. of xylene is distilled off. After cooling, 570 g. of phosphorus pentoxide is added along with sufficient dry xylene to facilitate stirring. This mixture is stirred at reflux for 17 hours, cooled and filtered. The filter cake is washed well with xylene, then with ether. The filtrates are combined and concentrated to an oil which crystallizes on trituration with hexane yielding 9-chloro-11-keto-6,11-dihydrodibenzo[b,e]oxepine, m.p. 82°–83° C.

To the Grignard reagent obtained from 4-chloro-N-methylpiperidine (0.70 mol) and magnesium (0.54 mol) in tetrahydrofuran is added 0.38 mol of the above oxepinone in 750 ml. of tetrahydrofuran at a rate sufficient to maintain a gentle reflux. The mixture is refluxed for about 90 minutes and stirred at room temperature overnight. the reaction mixture is poured over ice, treated with ammonium chloride and extracted several times with ether. The combined ether fractions are dried and concentrated to give 9-chloro-11-(1-methyl-4- piperidyl)-6,11-dihydrodibenzo[b,e]oxepine-11-ol, hydrochloride salt, m.p. 150°–160° C.

The above oxepinol (0.5 mol) is stirred with o-sulfobenzoic anhydride (1.15 mol) and propionic acid (3400 ml.). The mixture is heated on a steam bath for one hour, cooled, basified and extracted with methylene chloride. The organic extract is dried and concentrated in vacuo to an oil which is chromatographed on silica gel eluted with chloroform. The collected oil crystallizes when triturated with petroleum ether to yield 4-(9-chloro-11(6H)-dibenz[b,e]oxepinylidene)-1-methylpiperidine, m.p. 145°–146° C.; hydrochloride salt, m.p. 289° C. (dec.).

EXAMPLE 14

A solution of cyanogen bromide (14.1 g., 0.133 mol) in benzene (200 ml) at 35° C. is treated with a solution of 4-(2-chloro-9-xanthenylidene)-1-methylpiperidine (31.2 g., 0.10 mol) in benzene (250 ml.) over 15 minutes. The solution is heated to 55° C. for four hours. The solvent is evaporated and the residue is recrystallized from ethanol to give 4-(2-chloro-9-xanthenylidene)-1-cyanopiperidine, m.p. 148°–150° C. A solution of the latter (27.2 g., 0.084 mol) in glacial acetic acid (450 ml.), water (250 ml.) and concentrated hydrochloric acid is refluxed for 18 hours, and the major portion of the solvent is evaporated. The residue is basified and extracted with ethylacetate. The extracts are washed with water and the solvent evaporated. The residue is triturated with ethanol, filtered and the filtrate is evaporated to leave 4-(2-chloro-9-xanthenylidene)piperidine. The free base is dissolved in acetonitrile and treated with one equivalent of methanesulfonic acid to yield 4-(2-chloro-9-xanthenylidene)piperidine methanesulfonate, m.p. 256°–260° C.

EXAMPLE 15

A solution of 4-(2-chloro-9-xanthenylidene)piperidine (1.5 g., 5 mmol) in 50 ml. of methanol at 0° C. is treated with ethylene oxide (5 ml.). The solution is allowed to come to 23° C., then heated to 40° C. for one hour and the solvent evaporated. The residue is dissolved in acetonitrile and treated with one equivalent of methanesulfonic acid to give 4-(2-chloro-9-xanthenylidene)-1-($\beta$-hydroxyethyl)-piperidine methanesulfonate, m.p. 242°–244° C.

EXAMPLE 16

A solution of 4-(2-chloro-9-xanthenylidene)piperidine (3.8 g., 12.8 mmol) and 2 ml. of triethylamine in 75 ml. of benzene is treated with a solution of cyclobutylcarboxylic acid chloride (1.9 g., 16 1 mmol) in benzene (25ml.). After two hours at 23° C. the mixture is washed with water, 1N hydrochloric acid and 5% potassium carbonate. The organic solution is dried and evaporated to leave the intermediate amide. The solution of the amide (4.95 1 g.) in 75 ml. of ether is added to a stirred slurry of lithium aluminum hydride (3.0 g.) in ether (30 ml.). The mixture is refluxed for six hours and stirred at 23° C. for 2 days. Excess hydride is decomposed by the cautious addition of 6 ml. of water and 4.8 ml. of 10% sodium hydroxide and the solid is filtered. The filtrate is treated with ethereal hydrogen chloride and the precipitated salt is dissolved in a mixture of water and benzene. The water is separated, washed with ether, basified, and extracted with ether. The dried extract is evaporated and the residue is chromatographed on an alumina column, eluting with ether. The first fraction is evaporated to give 4-(2-chloro-9-xanthenylidene)-1-cyclobutylmethylpiperidine. A solution of the free base in acetonitrile is treated with one equivalent of methanesulfonic acid to obtain the methanesulfonate salt, m.p. 196°–197° C.

EXAMPLE 17

A mixture of 4-(2-bromo-9-xanthenylidene)-1-methylpiperidine (7.0 g., 19.7 mmol), cuprous cyanide (3.5 g.), cupric sulfate pentahydrate (50 mg.) and sodium cyanide (50 mg.) in 60 ml. of dimethylformamide is refluxed for 18 hours. The reaction mixture is poured into 10% aqueous sodium cyanide (500 ml.) and extracted with ether. The extract is washed with 10% aqueous sodium cyanide, water, dried and the solvent is evaporated. The residue is chromatographed on an alumina column, eluting with ether. The second fraction gives the product as an oil which is dissolved in ethanol and treated with one equivalent of furmaric acid, yielding 4-(2-cyano-9-xyanthenylidene) 1-methylpiperidine fumarate, m.p. 238°–241° C. (dec.).

EXAMPLE 18

A solution of 4-(2-chloro-9-xanthenylidene)piperidine (2.0 g., 6.75 mmol) in 5 ml. of acetic anhydride is heated on a steam bath for 2.5 hours. Acetone (30 ml.) and 50 ml. and 20% aqueous potassium carbonate is added to the cooled solution and the mixture stirred for one hour. Additional water is added and the mixture is extracted with ether. The extract is washed with 1N hydrochloric acid, water and dried. The solvent is evaporated to give the crude amide, 2.2 g. (recrystallized amide m.p. 165°–166° C.). The amide is dissolved in 500 ml. of ether and added to a stirred suspension of 2.0 g. of lithium aluminum hydride in 200 ml. of ether. After two hours at 23° C. excess hydride is decomposed with water (4 ml.) and 10% sodium hydrixode (3.2 ml.). The mixture is filtered and the filtrate is evaporated. The residue is dissolved in a mixture of methanol and ether and treated with one equivalent of methanesulfonic acid. The precipitated salt is filtered and recrystallized from methanol/ether to give 4-(2-chloro-9-xanthenylidene)-1-ethylpiperidine methanesulfonate, m.p. 249°–252° C.

EXAMPLE 19

A solution of 4-(2-chloro-9-xanthenylidene)piperidine (3.2 g., 10.8 mmol) and propyliodide (5 ml.) in dimethylformamide (25 ml.) is stirred at 23° C. for three hours and at 100° C. for one hour. The reaction mixture is diluted with water and extracted with ether. The extract is washed with water, dried and the solvent evaporated. The residue is chromatographed on an alumina column, using ether as the eluent. The first fraction gives the product which is converted to the hydrochloride salt: 4-(2-chloro-9-xanthenylidene)-1-propylpiperidine hydrochloride, m.p. 238°–240° C.

EXAMPLE 20

A mixture of 4.4 g. of 4-fluoroanthranilic acid in 35 ml. of water and 7 ml. of hyrochloric acid is diazotized with 2.0 g. of sodium nitrite in 6 ml. of water at 0°–5° C. The resulting cold solution is added dropwise to a mixture of 7.1 g. of potassium iodide, 2 ml. of sulfuric acid and 10 ml. of water. The mixture is heated for 2 hours to 100° C. and steam distilled. The cooled residue gives 4-fluoro-2-iodobenzoic acid, m.p. 140°–147° C.

A mixture of 4.7 g. of the above prepared benzoic acid, 1.93 g. of thiophenol, 3.62 g. of potassium carbonate and a catalytic amount of copper powder is stirred for one hour with 50 ml. of nitrobenzene at 160°–165° C. The cooled reaction mixture is poured into 100 ml. of water, strongly acidified, and extracted with chloroform. The extract is washed with water, decolorized with charcoal and filtered. The filtrate is extracted with 5% sodium bicarbonate solution. Acidification of the aqueous solution, followed by extraction with ether and subsequent evaporation of the dried extract yields 4-fluoro-2-(phenylthio)benzoic acid, m.p. 193°–200° C.

This benzoic acid (3 g.) is heated for one hour on a steam bath with 45 g. of sulfuric acid. The solution is poured onto ice, filtered and the solid is washed with water, then stirred with 5% sodium bicarbonate solution. The solid is filtered, washed with water and dissolved in chloroform. Evaporation of the dried chloroform solution furnishes 3-fluoro-9-thioxanthone, m.p. 168° C.

The Grignard reagent prepared from 0.62 g. of magnesium turnings and 3.5 g. of 4-chloro-N-methylpiperidine in tetrahydrofuran is treated with a solution of 3-fluoro-9-thioxanthone (3.0 g.) in 50 ml. of tetrahydrofuran. The mixture is refluxed for four hours, cooled, treated with saturated ammonium chloride solution and extracted with ether. The ether extract is washed with water, dried and concentrated to give 3-fluoro-9-(1-methyl-4-piperidyl)-thioxanthene-9-ol, m.p. 120°–130° C.

The thioxanthene-9-ol (3.2 g.) is dehydrated by refluxing for one hour with 3.68 g. of o-sulfobenzoic anhydride and 60 ml. of propionic acid. The cooled reaction mixture is poured into a mixture of ice and 40% sodium hydroxide solution, then extracted with ether. The dried extract is decolorized with charcoal, concentrated and the residue, dissolved in ether, is treated with maleic acid to yield 4-(3-fluoro-9-thioaxanthenylidene)-1-methylpiperidine maleate, m.p. 162°–164° C.

Similarly, 2-fluoro-9-thioxanthone (5.0 g.) is reacted with the Grignard reagent derived from 1.06 g. of magnesium turnings and 5.85 g. of 4-chloro-N-methylpiperidine in tetrahydrofuran as described above to give the corresponding 2-fluoro-9-(1-methyl-4-piperidyl)-thioxanthene-9-ol, m.p. 189°–190° C. The latter is dehydrated by the same procedure to obtain 4-(2-fluoro-9-thioxanthenylidene)-1-methylpiperidine as the maleate salt, m.p. 175°–179° C.

EXAMPLE 21

To a solution of 1.28 g. (0.01 mol) of p-fluorothiophenol and 2.82 g. (0.01 mol) of 2-iodo-4-chlorobenzoic acid in 20 ml. of pyridine is added 1.3 g. (0.01 mol) of potassium carbonate, with stirring. Additional pyridine is added until solution is clear and then 0.3 g. of cuprous chloride is introduced. The resulting mixture is refluxed overnight, poured into ice-water, stirred and filtered. The aqueous solution is acidified and filtered. The solid is dissolved in 5% sodium bicarbonate solution and this solution is extracted with ether. The aqueous solution is acidified, extracted with ether and the washed, dried extract is concentrated to give 4-chloro-2-(4-fluorophenylthio)-benzoic acid, m.p. 204°–213° C. The latter (6.5 g., 0.023 mol) is heated for one hour with 105 g. of sulfuric acid to obtain 2-fluoro-6-chloro-9-thioxanthone, m.p 222°–224° C.

The Grignard reagent prepared from 5.9 g. (0.044 mol) of 4-chloro-N-methylpiperidine and 1.1 g. (0.044 mol) of magnesium turnings of tetrahydrofuran is treated with 5.8 g. (0.022 mol) and the above-prepared thioxanthone. The mixture is refluxed for four hours and worked up by the usual procedure to yield 6-chloro-2-fluoro-9-(1-methyl-4-piperidyl)-thioxanthene-9-ol, m.p. 133°–142° C.

Dehydration is accomplished by heating 6.4 g. (0.018 mol) of the above thioxanthene-9-ol for one hour with 6.5 g. (0.035 mol) of o-sulfobenzoic anhydride in 100 ml. of propionic acid. Workup the reaction mixture affords 4-(6-chloro-2-fluoro-9-thioxanthenylidene) 1-methylpiperidine, isolated as the hydrochloride salt, m.p. 264°–265° C.

EXAMPLE 22

Following the procedures outlined in Example 21, 10.7 g. (0.038 mol) of 2-iodo-4-chlorobenzoic acid, 4.3 g. (0.038 mol) of 4-fluorophenol 5.25 g. (0.038 mol) of potassium carbonate and 1.14 g. of cuprous chloride in 180 ml. of pyridine are heated under reflux overnight to give upon workup 4-chloro-2-(4-fluorophenoxy)-benzoic acid, 154°–173° C. Heating the acid (5.0 g., 0.019 mol) for one hour with 75 g. of sulfuric acid yields the corresponding 2-fluoro-6-chloro-9-xanthone, m.p. 210° C.

Reaction of the xanthone (4.9 g., 0.0197 mol) with the Grignard reagent derived from 5.3 g. (0.039 mol) of 4-chloro-N-methylpiperidine and 0.95 g. (0.039 mol) Mg in tetrahydrofuran furnishes upon workup 6-chloro-2-fluoro-9-(1-methyl-4-piperidyl)-xanthene-9-ol, m.p. 107°–127° C.

The xanthene-9-ol (1.7 g., 0.0049 mol) is dehydrated by heating for one hour with o-sulfobenzoic anhydride (1.8 g., 0.0098 mol) in 35 ml. of propionic acid. The product is isolated as its hydrochloride salt, 4-(6-chloro-2-fluoro-9-xanthenylidene)-1-methylpiperidine hydrochloride, m.p. 235° C.

EXAMPLE 23

To a solution of 3.28 g. (0.0256 mol) of p-fluorothiophenol and 6.8 g. (0.0256 mol) of 2-iodo-4-fluorobenzoic acid in 40 ml. of pyridine is added 3.54 g. (0.0256 mol) of potassium carbonate at room temperature with stirring. Additional pyridine is added to dissolve the precipitate and then 1.54 g. of cuprous chloride is added. The mixture is refluxed overnight, cooled, poured into ice-water, stirred and filtered. The aqueous solution is acidified, filtered and the solid dissolved in 5% sodium bicarbonate solution, then extracted with ether. The aqueous solution is acidified, extracted with ether, and the dried extract is concentrated to give 4-fluoro-2-(4-fluorophenylthio)benzoic acid, m.p. 209°–218° C. The latter (3.0 g., 0.0113 mol) is cyclized by heating for one hour with 45 g. of concentrated sulfuric acid to obtain 2,6-difluorothioxanthone, m.p. 205°–210° C.

The Grignard reagent prepared from 2.7 g. (0.02 mol) of 4-chloro-N-methylpiperidine and 0.5 g. (0.02 mol) of magnesium turnings in tetrahydrofuran is treated with 2.5 g. (0.01 mol) of 2,6-difluorothioxanthone at a rate to maintain slow reflux. The mixture is refluxed for six hours, hydrolyzed with saturated ammonium chloride solution and extracted with ether to yield 2,6-difluoro-9-(1-methyl-4-piperidyl)-thioxanthene-9-ol, m.p. 207°–209° C.

The thioxanthene-9-ol (2.6 g., 0.0075 mol) prepared as above is heated with 2.8 g. (0.015 mol) of o-sulfobenzoic anhydride in 80 ml. of propionic acid. The product is isolated by the usual procedure to give 4-(2,6- difluoro-9-thioxanthenylidene)-1-methylpiperidine, m.p. 120°–123° C.

EXAMPLE 24

Sodium hydride (0.1 mol) is suspended in 60 ml. of dry dimethylformamide and 0.1 mol of 3-chlorophenol in about 60 ml. of dimethylformamide is added dropwise maintaining the temperature at 25° C. When hydrogen evolution is completed, 0.1 mol of phthalide in about 60 ml. of dimethylformamide is added slowly at 25° C. The mixture is refluxed for two hours, stirred at room temperature overnight, poured into ice-water and extracted with ether. The aqueous fraction is acidified with concentrated hydrochloric acid and extracted with ether. The combined ether fraction is dried and concentrated to give 2-(3-chlorophenoxymethyl) benzoic acid, m.p. 154°–155° C.

Following the procedure of Example 13, the above prepared benzoic acid is cyclized with phosphorus pentoxide in xylene to furnish 3-chloro-11-keto-6,11-dihydrodibenz[b,e]oxepine, m.p. 105°–106° C.

To the Grignard reagent prepared from 0.54 mol of magnesium and 0.7 mol of 4-chloro-N-methylpiperidine in tetrahydrofuran is added 0.38 mol of the 11-keto dibenzoxepine prepared above in tetrahydrofuran. The mixture is refluxed three hours, stirred at room temperature overnight, poured into ice-water, treated with ammonium chloride and extracted with ether. The ether extract is dried and concentrated in vacuo to yield 3-chloro-11-(1-methyl-4-piperidyl)-6,11-dihydrodibenz[b,e]oxepine-11-ol, m.p. 199°–200° C.

A mixture of 0.1 mol of the above oxepinol and 0.2 mol of o-sulfobenzoic anhydride in about 1200 ml. of propionic acid is stirred on a steambath for about 45 minutes. The cooled reaction mixture is poured over ice, basified with 30% sodium hydroxide solution and extracted with chloroform. The dried extract is concentrated to give 4-(3-chloro-11(6H)-dibenz[b,e]oxepinylidene)-1-methylpiperidine, m.p. 113°–116° C.

EXAMPLE 25

A mixture of 5.0 g. (13.5 mmol) of 4-(2-bromo-9-thioxanthenylidene)-1-methylpiperidine (prepared as in Example 10) and 2.42 g. (27 mmol) of cuprous cyanide in 30 ml. of dimethylformamide is refluxed with stirring for 18 hours. The reaction mixture is poured into 10% aqueous sodium cyanide and extracted with ether. The extract is washed with water, dried and the solvent evaporated. The residue is chromatographed over an alumina column using ether as the eluent. The first fraction is evaporated, the residue is dissolved in ethanol and the solution is treated with one equivalent of fumaric acid to precipitate 4-(2-cyano-9-thioxanthenylidene)-1-methylpiperidine fumarate salt, m.p. 211°–215° C.

EXAMPLE 26

A solution of 3.5 g. (11.8 mmol) of 4-(2-chloro-9-xanthenylidene)piperidine (prepared as in Example 14), 2.0 g. (13.4 mmol) of 3-bromo-1-propanol and 50 mg. of potassium iodide in 50 ml. of dimethylformamide is stirred at 23° C. for 18 hours and 100° C. for 12 hours. The reaction mixture is poured into water, basified and extracted with a mixture of ether and ethyl acetate. The extract is washed with water, dried and the solvent evaporated. The residue is chromatographed on an alumina column using ethyl acetate-ether 1:1 as the eluent. The first fraction yields the product which is treated with ethereal hydrogen chloride to give 4-(2-chloro-9-xanthenylidene)-1-(3-hydroxypropyl)piperidine hydrochloride, m.p. 225°–258° C.

EXAMPLE 27

A mixture of 2.0 g. (0.0058 mol) of 4-(2-bromo-9-xanthenylidene)piperidine (prepared as in Example 9), 0.89 g. (0.70 ml., 0.0065 mol) of n-butyl bromide and a few crystals of potassium iodide in 15 ml. of dimethylformamide is heated at 90°–95° C. for 2.5 hours under argon. The reaction mixture is poured into water, basified with sodium carbonate and extracted with ether. The extract is washed with water, dried and evaporated to an oil which is chromatographed over alumina with chloroform to give an oil which is converted to a methanesulfonic acid salt of the product 4-(2-bromo-9-xanthenylidene)-1-n-butylpiperidine, m.p. 199°–200° C.

EXAMPLE 28

To a solution of 18.6 g. (0.176 mol) of cyanogen bromide in 200 ml. of dry benzene at 50° C. is added gradually over four hours a solution of 57.9 g. (0.168 mol) of 1-methyl-4-(2-trifluoromethyl-9-xanthenylidene)piperidine. The reaction mixture is heated and stirred for 1.5 hours, excess water is added and the benzene solution is extracted with excess dilute acetic acid. The acetic acid extract is washed with water and the benzene solution is evaporated to give the 1-cyano intermediate. The latter (20 g., 0.0561 mol) is refluxed for 18 hours with a solution of 420 ml. of acetic acid, 280 ml. of water and 42 ml. of concentrated hydrochloric acid. The reaction mixture is concentrated in vacuo to about 125 ml., diluted with 400 ml. of water and extracted with ether. The aqueous layer is basified with excess sodium hydroxide solution and the mixture is extracted with ether. Concentration of the ether extract yields 4-(2-trifluoromethyl-9-xanthenylidene)piperidine.

A mixture of 4.0 g. (0.0121 mol) of the above prepared piperidine and 15 ml. of butyric anhydride is refluxed 2–3 hours. The reaction mixture is cooled, washed and stirred with an excess of 20% aqueous potassium carbonate-acetone for three hours. This mixture is extracted with ether and azeotroped with toluene. The crude amide (5.0 g.) is dissolved in 30 ml. of ether and gradually added to 0.9 g. (0.025 mol) of lithium aluminum hydride in 100 ml. of ether, with stirring. The mixture is stirred at room temperature overnight, decomposed with 1.8 ml. of water added slowly and filtered. The solid is treated with ethereal hydrogen chloride to give 1-n-butyl-4-(2-trifluoromethyl-9-xanthenylidene)piperidine hydrochloride, m.p. 251°–252° C.

EXAMPLE 29

A solution of 4-(2-chloro-9-xanthenylidene)-1-methylpiperidine in acetonitrile is treated with one equivalent of methanesulfonic acid to give the corresponding methanesulfonate salt, m.p. 225°–228° C.

What is claimed is:

1. A compound represented by one of the formulas:

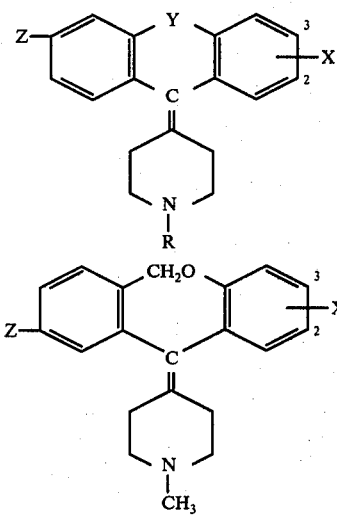

FORMULA I

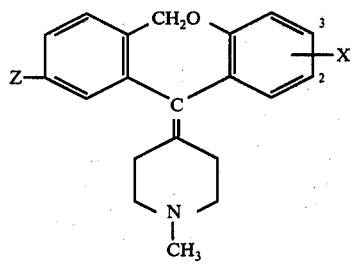

FORMULA II wherein, for formula I:
when Y represents oxygen, X is 2-fluoro, Z is 6-chloro and R is methyl;
when Y represents sulfur, X is 2-cyano, Z is hydrogen and R is methyl; and
for formula II:
when X is hydrogen, Z is 9-chloro, or a nontoxic pharmaceutically acceptable acid addition salt thereof.

2. A compound according to claim 1, of formula I, in which Y is oxygen, X is 2-fluoro, Z is 6-chloro and R is methyl.

3. A compound according to claim 1, of formula I, in which Y is sulfur, X is 2-cyano, Z is hydrogen and R is methyl.

4. A compound according to claim 1, of formula II, in which X is hydrogen and Z is 9-chloro.

5. A pharmaceutical composition having antipsychotic activity without producing extrapyramidal symptoms in dosage unit form which comprises a pharmaceutically carrier and a compound selected from among 4-(2-chloro-9-xanthenylidene)-1-methylpiperidine, 4-(6-chloro-2-fluoro-9-xanthenylidene)-1-methylpiperidine, 4-(2-cyano-9-thioxanthenylidene)-1-methylpiperidine and 4-(9-chloro-11(6H)-dibenz[b,e]oxepinylidene)-1-methylpiperidine, or a nontoxic pharmaceutically acceptable acid addition salt of said compound, in a nontoxic amount sufficient to produce said activity.

6. A pharmacuetical composition according to claim 5 in which the compound is 4-(2-chloro-9-xanthenylidene)-1-methylpiperidine.

7. A pharmaceutical composition according to claim 6 in which the compound is in the form of a methanesulfonate salt.

8. A pharmaceutical composition according to claim 5 in which the active ingredient is in an amount selected from about 1 mg. to about 300 mg. per dosage unit.

9. A pharmaceutical composition according to claim 5 in which the active ingredient is in an amount selected from about 5 mg. to about 200 mg. per dosage unit.

10. A method of producing antipsychotic activity without extrapyramidal symptoms which comprises administering internally to an animal in need of such activity a therapeutically effective amount of a compound represented by one of the formulas:

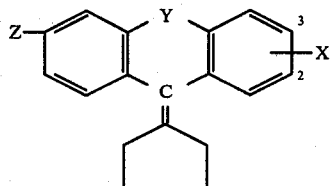

FORMULA I

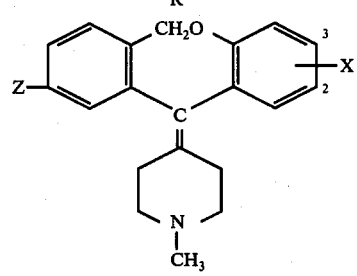

FORMULA II wherein, for formula I:
when Y represents oxygen, X is 2-chloro, Z is hydrogen and R is methyl;
when Y represents sulfur, X is 2-cyano, Z is hydrogen and R is methyl;
when Y represents oxygen, X is 2-fluoro, Z is 6-chloro and R is methyl;
for formula II:
when X is hydrogen, Z is 9-chloro, or a nontoxic pharmaceutically acceptable acid addition salt thereof.

11. A method according to claim 10 in which the compound is 4-(2-chloro-9-xanthenylidene)-1-methylpiperidine.

12. A method according to claim 11 in which the compound is in the form of a methanesulfonate salt.

13. A method according to claim 10 in which the compound is administered with a pharmaceutical carrier in dosage unit form.

14. A method according to claim 13 in which the administration is orally.

15. A method according to claim 13 in which the administration is intramuscularly.

16. A method according to claim 13 in which an active, nontoxic quantity selected from about 1 mg. to about 300 mg. of the compound is administered.

17. A method according to claim 10 in which a daily dosage selected from about 2 mg. to about 900 mg. of the compound is administered.

* * * * *